United States Patent
Clarke et al.

(10) Patent No.: US 11,612,500 B2
(45) Date of Patent: Mar. 28, 2023

(54) SET OF TOOLS FOR INSTALLING AN IMPLANT

(71) Applicant: Loci Orthopaedics Limited, Galway (IE)

(72) Inventors: Gerry Clarke, County Galway (IE); Fiona Mangan, County Limerick (IE); Filip Stockmans, Heule Kortrijk (BE); Arnold-Peter C. Weiss, Barrington, RI (US); Amy L. Ladd, Stanford, CA (US); Brendan Boland, County Kildare (IE)

(73) Assignee: Loci Orthopaedics Limited, Galway (IE)

( * ) Notice: Subject to any disclaimer, the term of this patent is extended or adjusted under 35 U.S.C. 154(b) by 0 days.

(21) Appl. No.: 17/833,246

(22) Filed: Jun. 6, 2022

(65) Prior Publication Data
US 2022/0296389 A1  Sep. 22, 2022

Related U.S. Application Data

(63) Continuation of application No. 17/604,300, filed as application No. PCT/EP2020/061558 on Apr. 24, 2020.
(Continued)

(51) Int. Cl.
*A61B 17/88* (2006.01)
*A61B 17/16* (2006.01)
(Continued)

(52) U.S. Cl.
CPC .......... *A61F 2/4606* (2013.01); *A61B 17/164* (2013.01); *A61B 17/1659* (2013.01);
(Continued)

(58) Field of Classification Search
None
See application file for complete search history.

(56) References Cited

U.S. PATENT DOCUMENTS

| 4,995,875 A | 2/1991 | Coes |
| 5,324,293 A | 6/1994 | Rehmann |

(Continued)

FOREIGN PATENT DOCUMENTS

| DE | 7146205 U | 3/1972 |
| DE | 60025954 T2 | 8/2006 |

(Continued)

OTHER PUBLICATIONS

International Search Report in International Application No. PCT/EP2020/061558, dated Nov. 11, 2020 (4 pages).

*Primary Examiner* — Ann Schillinger
(74) *Attorney, Agent, or Firm* — Bookoff McAndrews, PLLC

(57) ABSTRACT

A set of tools for installation of a stem implant into a bone comprises a stem-shaped priming tool (1) having a distal tip (32) and a plurality of cutting teeth (31) along a length thereof and a plurality of stem-shaped broaches (2, 3, 4, 5, 6) of different size. Each of the broaches have a distal tip and a plurality of cutting teeth along a length thereof. The priming tool (1) is shorter than, has more cutting teeth (31) per unit length, and has a sharper distal tip (32) than the smallest broach.

24 Claims, 13 Drawing Sheets

Related U.S. Application Data

(60) Provisional application No. 62/847,689, filed on May 14, 2019.

(51) Int. Cl.
  *A61B 17/32* (2006.01)
  *A61F 2/46* (2006.01)
  *A61B 50/20* (2016.01)
  *A61B 50/33* (2016.01)
  *A61B 17/00* (2006.01)
  *A61F 2/42* (2006.01)
  *A61B 50/00* (2016.01)
  *A61B 17/92* (2006.01)
  *A61F 2/30* (2006.01)

(52) U.S. Cl.
  CPC .......... *A61B 17/1686* (2013.01); *A61B 50/20* (2016.02); *A61F 2/4684* (2013.01); *A61B 17/921* (2013.01); *A61B 50/33* (2016.02); *A61B 2017/00429* (2013.01); *A61B 2017/00464* (2013.01); *A61B 2017/00477* (2013.01); *A61B 2050/005* (2016.02); *A61F 2/4637* (2013.01); *A61F 2002/30607* (2013.01); *A61F 2002/4258* (2013.01)

(56) References Cited

U.S. PATENT DOCUMENTS

| | | | |
|---|---|---|---|
| 6,059,832 A | 5/2000 | Menon | |
| 6,206,884 B1* | 3/2001 | Masini | A61B 17/1659 606/89 |
| 6,656,187 B1* | 12/2003 | Camino | A61B 17/1659 606/85 |
| 8,579,985 B2* | 11/2013 | Podolsky | A61F 2/367 623/22.42 |
| 8,657,824 B2* | 2/2014 | Sharp | A61B 17/1604 606/80 |
| 9,474,561 B2* | 10/2016 | Shemwell | A61B 17/8888 |
| 9,962,173 B2* | 5/2018 | Thomas | A61F 2/389 |
| 10,166,031 B2* | 1/2019 | Witt | A61B 17/1668 |
| 11,172,939 B2* | 11/2021 | Donner | A61B 17/1739 |
| 2002/0016634 A1* | 2/2002 | Maroney | A61F 2/4014 623/22.42 |
| 2002/0091393 A1* | 7/2002 | Gundlapalli | A61B 17/1764 606/88 |
| 2004/0267266 A1* | 12/2004 | Daniels | A61B 17/162 606/80 |
| 2005/0234462 A1* | 10/2005 | Hershberger | A61F 2/4637 606/85 |
| 2005/0251263 A1 | 11/2005 | Forrer et al. | |
| 2005/0288676 A1* | 12/2005 | Schnieders | A61B 17/175 606/79 |
| 2007/0173945 A1 | 7/2007 | Wiley et al. | |
| 2009/0281631 A1 | 11/2009 | Naidu | |
| 2010/0076493 A1* | 3/2010 | Fauth | A61B 17/7032 606/279 |
| 2010/0268228 A1* | 10/2010 | Petersen | A61B 17/1757 606/60 |
| 2011/0015634 A1 | 1/2011 | Smith et al. | |
| 2012/0259338 A1 | 10/2012 | Carr et al. | |
| 2012/0265319 A1* | 10/2012 | Prybyla | A61F 2/34 623/22.36 |
| 2013/0053975 A1* | 2/2013 | Reed | A61B 17/8883 623/21.19 |
| 2014/0194999 A1 | 7/2014 | Orbay et al. | |
| 2014/0207200 A1* | 7/2014 | Kerboul | A61B 17/1659 606/86 R |
| 2014/0257495 A1 | 9/2014 | Goldberg | |
| 2014/0276850 A1* | 9/2014 | Chaney | A61F 2/461 606/84 |
| 2015/0039037 A1* | 2/2015 | Donner | A61B 17/1604 606/85 |
| 2016/0278818 A1* | 9/2016 | Donner | A61B 17/7043 |
| 2017/0035571 A1 | 2/2017 | Loffredo | |
| 2017/0209155 A1* | 7/2017 | Peteresen | A61B 17/025 |
| 2018/0028196 A1* | 2/2018 | Sharkey | A61B 17/1664 |
| 2018/0214233 A1* | 8/2018 | Termanini | A61B 50/20 |
| 2018/0250024 A1 | 9/2018 | Woodard et al. | |
| 2019/0099191 A1 | 4/2019 | Huff et al. | |
| 2019/0167375 A1* | 6/2019 | Niese | A61B 17/1659 |

FOREIGN PATENT DOCUMENTS

| | | | | |
|---|---|---|---|---|
| EP | 1080701 A2 * | 3/2001 | | A61F 2/3804 |
| EP | 1393697 A1 | 3/2004 | | |
| EP | 2147642 A2 | 1/2010 | | |
| EP | 2615988 A2 | 7/2013 | | |
| EP | 3413843 A2 | 12/2018 | | |
| JP | 2016010604 A * | 1/2016 | | |
| WO | WO 01/28469 A2 | 4/2001 | | |
| WO | WO 2012/037137 A2 | 3/2012 | | |
| WO | WO-2012037137 A2 * | 3/2012 | | A61B 17/1615 |
| WO | WO 2017/034845 A1 | 3/2017 | | |
| WO | WO 2017/137607 A2 | 8/2017 | | |
| WO | WO 2018/183168 A1 | 10/2018 | | |

* cited by examiner

Section A-A

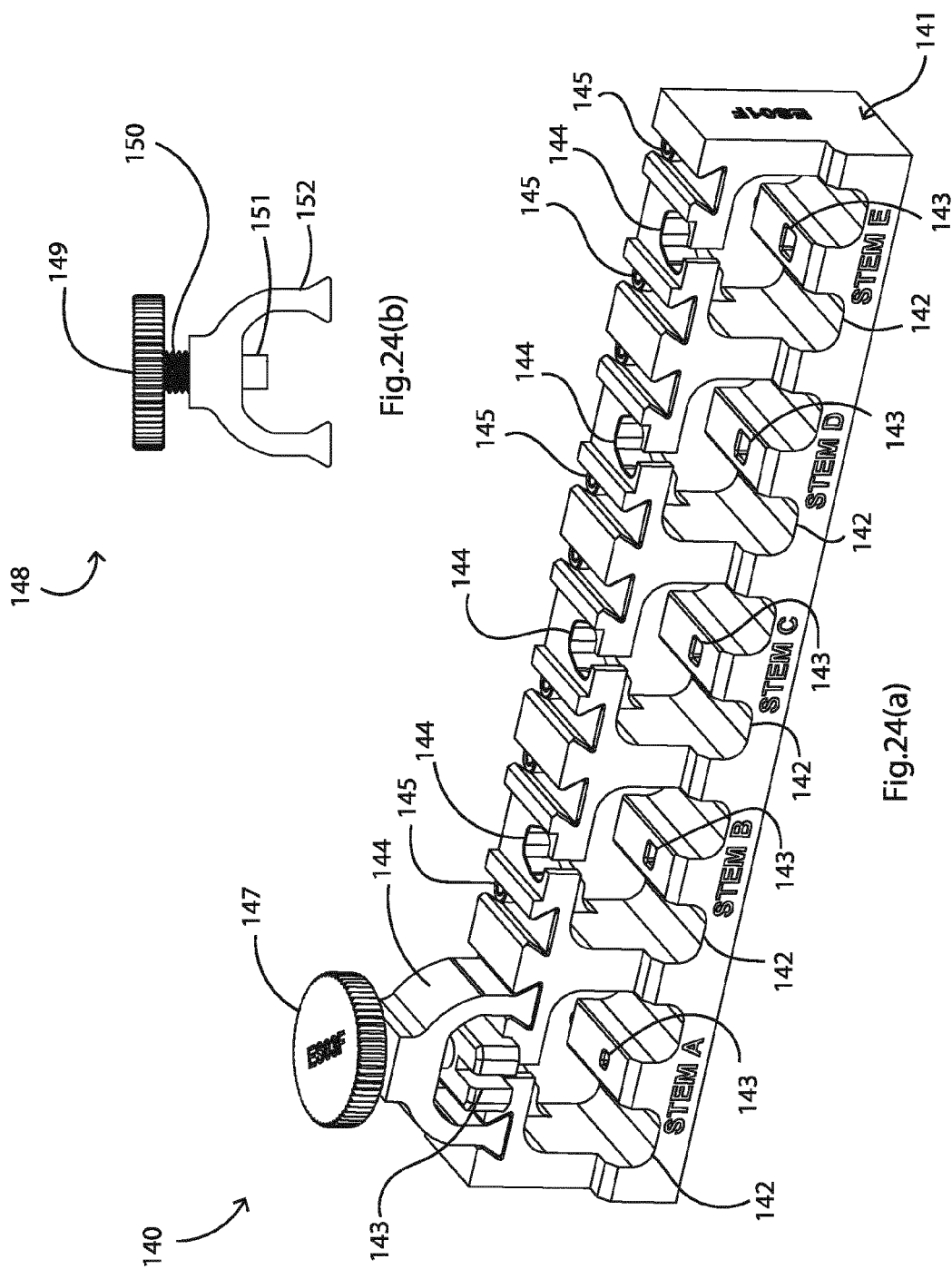

SET OF TOOLS FOR INSTALLING AN IMPLANT

CROSS-REFERENCE TO RELATED APPLICATIONS

This application is a continuation application under 37 C.F.R. § 1.53(b) of U.S. application Ser. No. 17/604,300, filed on Oct. 15, 2021, which is the US National Stage filing under 35 U.S.C. § 371 of International Application No. PCT/EP2020/061558, filed on Apr. 24, 2020, which claims the benefit of priority of U.S. Provisional Patent Application No. 62/847,689, filed on May 14, 2019, all of which are incorporated herein by reference in their entireties.

INTRODUCTION

The invention relates to tools for use by a surgeon in implant surgery.

All orthopaedic implants require a set of tools to enable installation of implant components. The set will comprise several trial fittings to establish the implant component sizes required for the patient, as well as a number of specific tools to facilitate the fixing of the implant in the patient's joint. The implant tool set will often be augmented in theatre by generic tools, readily found in orthopaedic surgical environments, such as impactors of various weights, osteotomes of various sizes, retractors of various types, K-wires and oscillating saws.

The invention is directed towards achieving improved efficiency in implant surgery.

Summary Statements

We describe a set of tools for installation of a stem implant into a bone. Also described are features of the set of tools. We also describe a kit comprising a set of tools as described for any example, and a stem implant. We also describe an apparatus for use in installing an implant comprising a set of tools of any example and a tray to house the tools. We also describe broaches of various examples. We also describe dual purpose tools of various examples. We also describe an assembly fixture in various examples.

According to the one aspect we describe a set of tools for installation of a stem implant into a bone, comprising:
- a stem-shaped priming tool having a distal tip and a plurality of cutting teeth along a length thereof; and
- a plurality of stem-shaped broaches of different sizes, each of the broaches having a distal tip and a plurality of cutting teeth along a length thereof,
- wherein the priming tool is shorter than, has more cutting teeth per unit length, and has a sharper distal tip than the smallest broach.

In one case the priming tool and the broaches comprise a plain proximal handle end having flutes to aid grip.

The priming tool and the broaches may comprise a flange distal of the proximal handle of the tool. The flange may be truncated on one side of the handle.

In some cases the distal head of the priming tool and the broaches are curved in a volar direction and are substantially flat in a dorsal direction.

The set of tools may further comprise a stem insertion tool having engagement features for engaging with corresponding engagement features of the implant stem for transmission of forces applied to the stem insertion tool directly to the stem implant.

The set of tools may further comprise at least one further tool which is a dual-purpose tool. The dual-purpose tool in one case has a head which provides both a rasp and a broach.

In another case the dual-purpose tool comprises a lever for elevation of a bone. The lever may comprise a distal engagement slot.

The set of tools as claimed may further comprise a stem exchange tool.

The set of tools may further comprise at least one trial head for temporary placement in a bone during preparation of the bone to receive an implant head. The trial head in one case has some dimensions that are smaller than those of an implant head. There may be a plurality of different sized trial heads.

Also provided is a kit comprising a set of tools of the invention and a stem implant. The stem implant may be configured for intramedullary engagement with an end of the first metacarpal bone. The implant in one case comprises an insert for a proximal end of the stem.

In one case the implant is for a first carpometacarpal joint for spacing a trapezium bone from a first metacarpal bone, the implant comprising a proximal implant part having a saddle-shaped surface for translational movement over the trapezium and the stem is mountable to the proximal part in an articulated coupling such as a ball and socket joint. The proximal part may comprise a head for mounting to the stem.

We also describe an apparatus for use in installing an implant comprising a set of tools of the invention and a tray to house the tools. The tray may comprise a base, side walls upstanding from the base, and tool support strips mounted to the base. In one case the tray comprises two support strips extending across the tray, each of the support strips comprising spaced-apart recesses to accommodate portion of the tools. The tools may be mounted to the strips in the order in which the tools are to be used in a surgical procedure. A lid for the tray may have a single strip projecting inwardly therefrom to engage the tools and retain their position in the tray.

Also provided is a broach for use in preparing a bone to receive an implant comprising a proximal handle, a shaft extending from the handle, and a flange between the handle and the shaft. In one case the flange is truncated on one side of the handle. The handle may comprise a plurality of generally flat sides having flutes to enhance grip. The distal head may be curved in the volar direction and substantially flat in a dorsal direction.

We also describe a dual purpose tool for remodelling bone to receive an implant comprising a handle, a shaft extending from the handle and a distal cutting head having a first side and a second side opposite to the first side, the first side of the cutting head having rasp features and the second side of the head having broach features. The first side in one case is of concave shape and the second side is of convex shape. The distal end of the tool may be of circular, square, flat or toroidal shape. In some cases, the handle comprises a plurality of generally flat sides and comprises flutes to aid grip.

We also describe a dual-purpose tool comprising a handle, a shaft extending from the handle and a distal tip, the shaft being angled with respect to the handle to facilitate manipulation of small bones and the distal tip having a slot to engage an element to facilitate leverage of the element. The shaft may be generally flat. The handle may comprise a plurality of generally flat sides and comprises flutes to aid grip.

The tool set contains specific tools, and tool features. These tools have been specifically designed for a particular implant, but their novel features also have applications in other areas of orthopaedic surgery.

BRIEF DESCRIPTION OF THE DRAWINGS

The invention will be more clearly understood from the following description thereof, given by way of example only, in which:

FIG. 13(b) is a cross-sectional side view and FIG. 13(c) is a diagrammatic enlarged sectional side view illustrating the stem insertion tool, in use;

FIG. 24(a) is a perspective view of an intraoperative assembly, and FIG. 24(b) is an end view of a component of the assembly.

DETAILED DESCRIPTION

Figure 1:
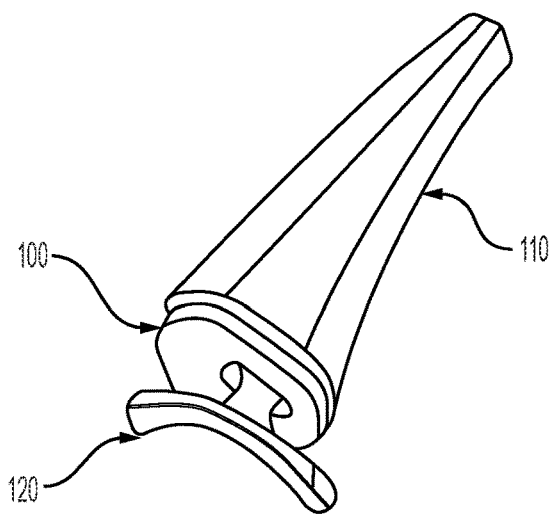
FIG. 1 is an image showing in perspective an implant comprising proximal and distal parts.
Figure 2A:
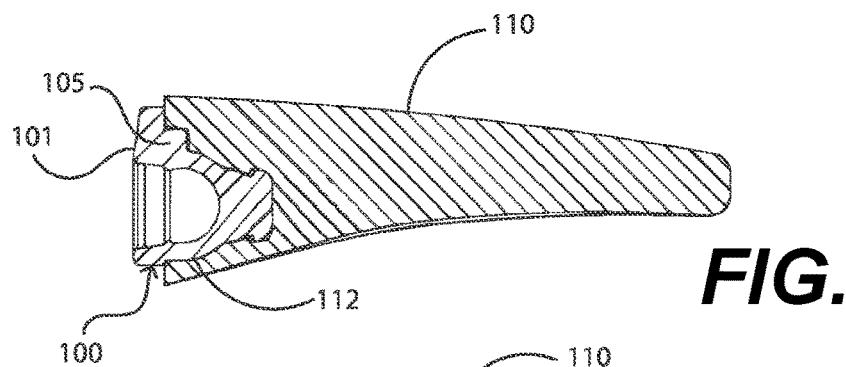
FIG. 2(a) is a cross-sectional view through the implant distal part.
Figure 2B:
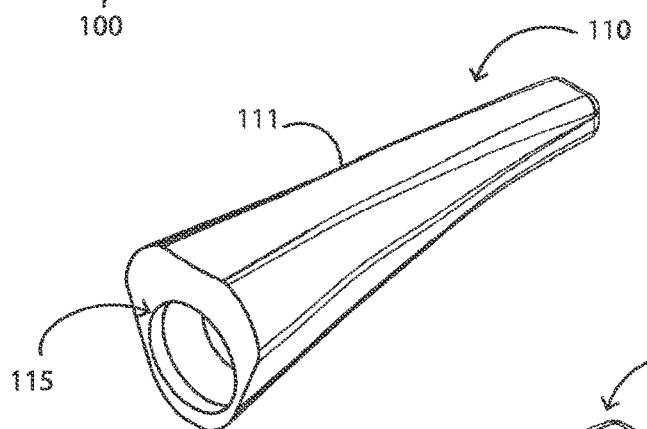
FIG. 2(b) is a perspective view of the stem of the distal part.
Figure 2C:
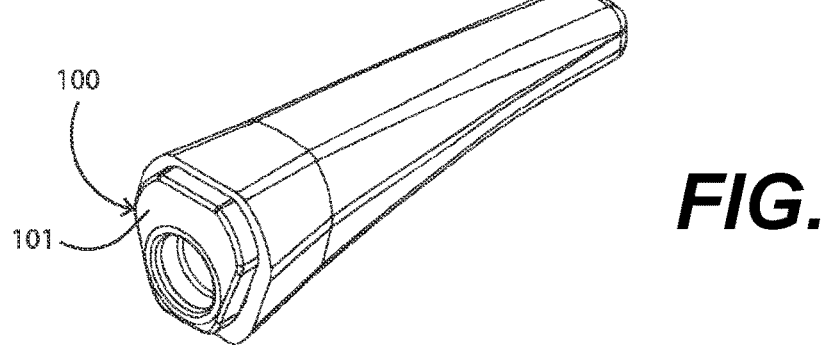
FIG. 2(c) is a perspective view of the complete distal part.
Figure 2D:
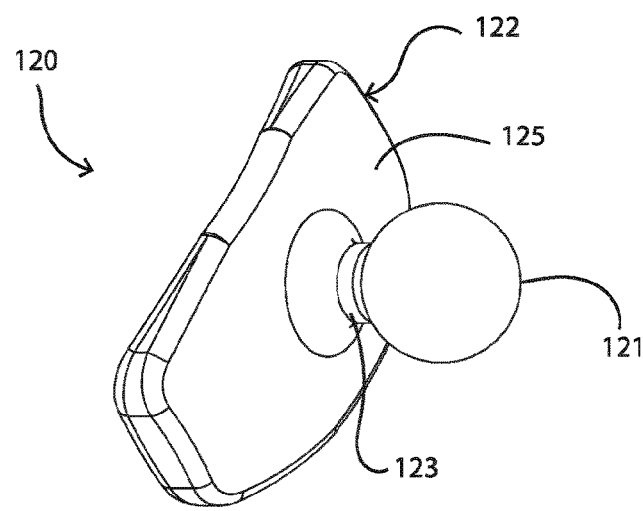
FIG. 2(d) is a perspective view of the proximal part.
Figure 3:
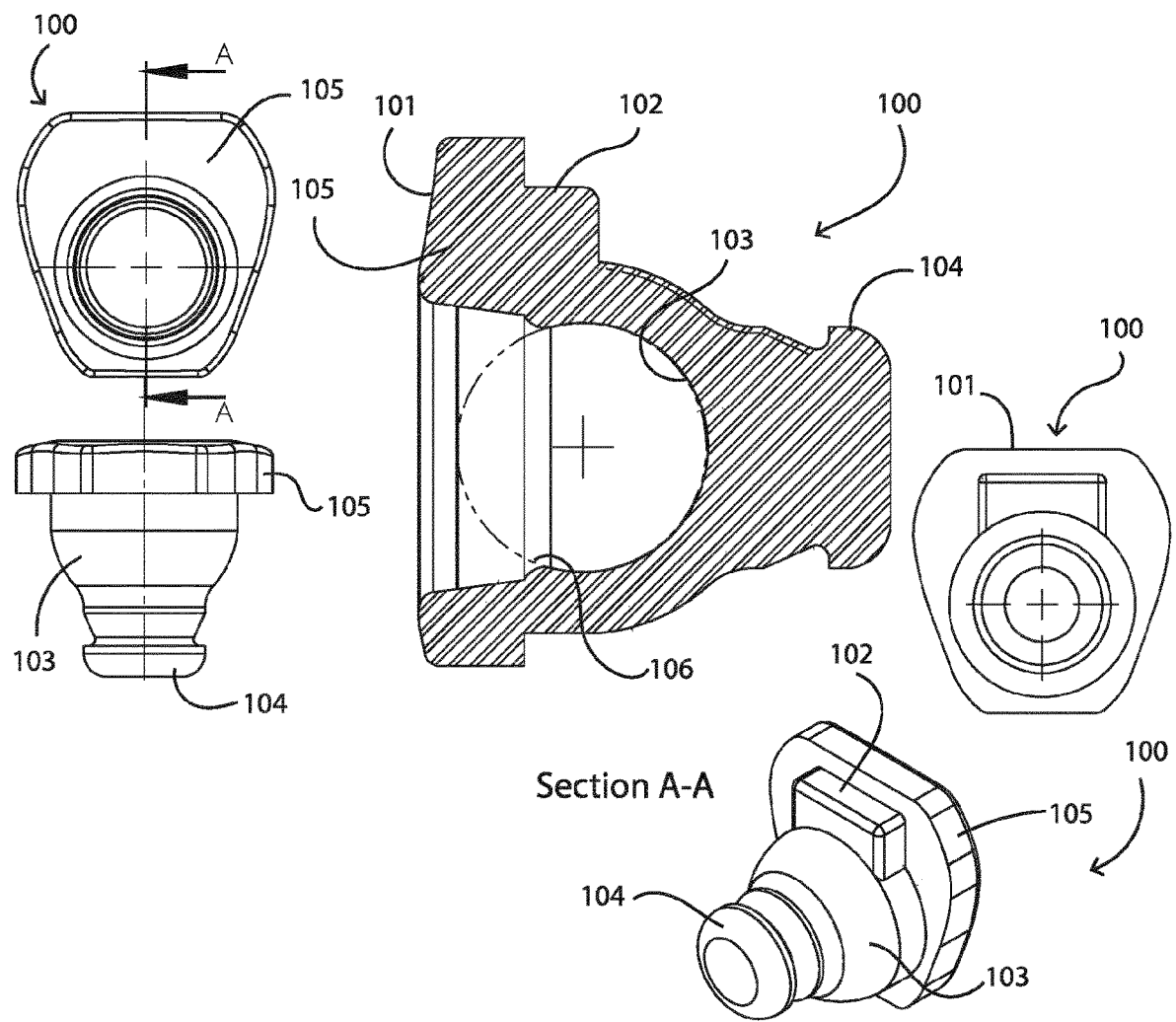
FIG. 3 is a set of views showing a portion of the distal part of the implant, including top plan, end, perspective, and cross-sectional views.

One example of an implant which may be installed using the set of tools of the invention is shown in FIGS. 1 to 3. Referring to FIGS. 1 to 3 an implant 1 has a distal part with an insert 100 in a stem 110, and a proximal part 120. In this case the implant 1 is for a mammalian first carpometacarpal joint for spacing a trapezium bone of the joint from a first metacarpal bone of the joint while allowing translational and rotational movement of the first metacarpal bone in relation to the trapezium bone. The distal part 110 is configured for intramedullary engagement with an end of the first metacarpal bone. The proximal part 120 has a curved saddle-shaped platform 122 with a proximal-facing surface 124 for sliding on or traversing the trapezium bone. An articulating coupling comprises a neck 123 bridging the saddle 122 to a ball 121, as is known. This allows controlled articulation of the trapezium and first metacarpal bones.

The insert 100 may have a buffer interface feature, in this case a flange 105 with a contoured proximally-facing surface 101. Distally of this surface there is a shoulder 102 which acts as a key for engaging the insert 100 in the stem 111 and preventing rotation of the insert in the stem, and surrounding a socket 103 with a rim 106 to receive the articulated coupler ball 121. There is snap-fit engagement of the ball 121 (see especially FIG. 2(d)) in the socket 103, behind the socket's rim 106, to enable the assembly of an articulating hemiarthroplasty intra-operatively, and it may also prevent disassembly of the device in vivo. The socket can be central or offset in any direction or angle as needed.

Further distally, the insert 100 comprises an annular locking rim 104 for snap-fitting into a corresponding groove of the stem 111 recess 115 which accommodates the insert 100. Engagement of the insert 100 into the stem 111 is effective due to the resilience of the insert material and the fact that there is comprehensive surface-to-surface contact in a snap-fitting manner between the rim 104 and its corresponding engagement surface within the stem 111. The insert is keyed by the shoulder 102 to prevent rotation and potential consequent back side wear.

Figure 4:
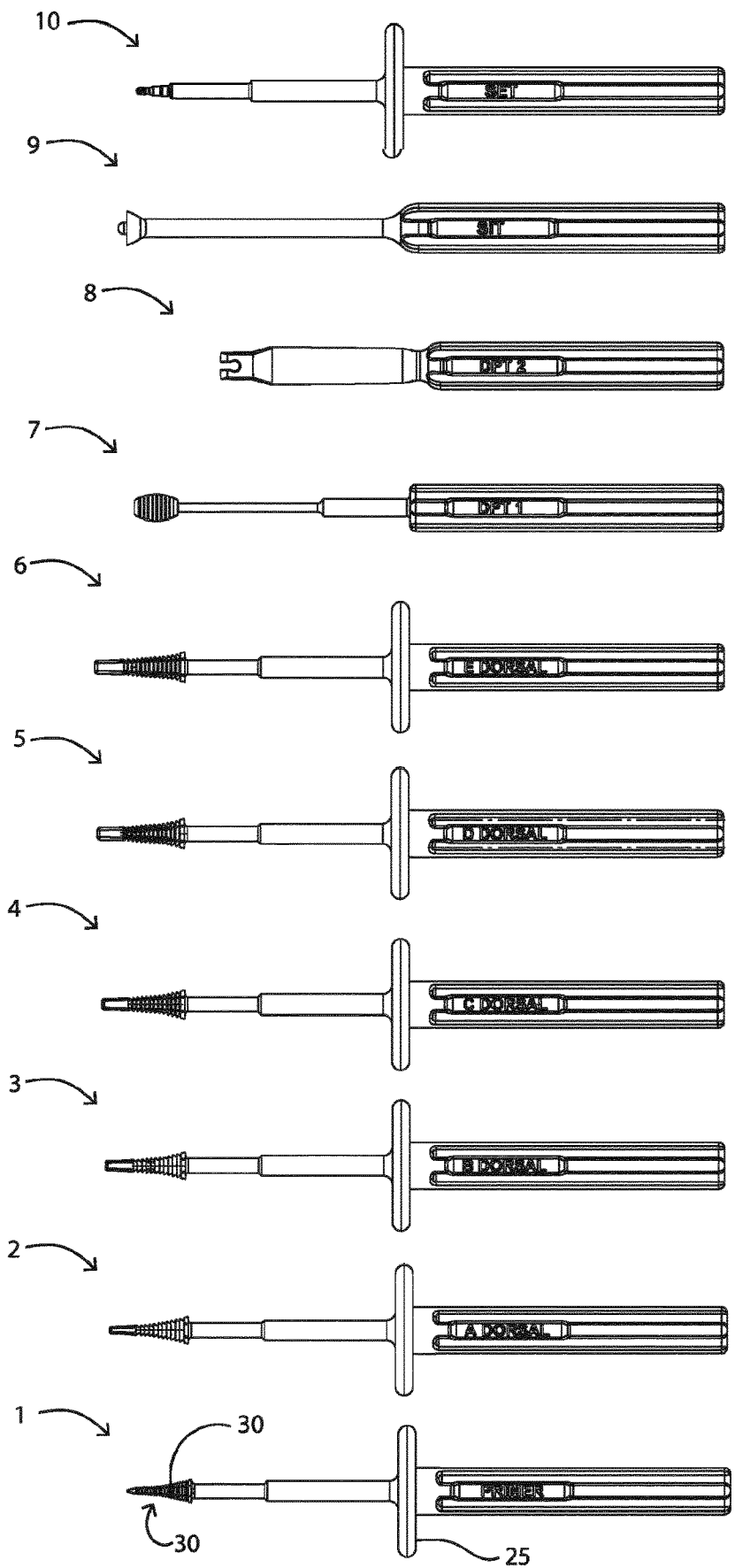
FIG. 4 illustrates a set of tools according to the invention in one example.

Referring to FIG. 4 there is illustrated a set of tools for use in installing an implant such as the implant of FIGS. 1 to 3. The set of tools in this example comprises:
- a primer 1 (FIGS. 5 and 6);
- a set of five broaches 2, 3, 4, 5, 6 of different size (FIG. 7);
- a first dual purpose tool 7 (FIGS. 8 and 9);
- a second dual purpose tool 8 (FIGS. 10, 11 and 12);
- a stem insertion tool 9 (FIGS. 13(a), 13(b), 13(c)); and
- a stem exchange tool 10 (FIG. 141(a), 14(b), 14(c)).

Figure 5:
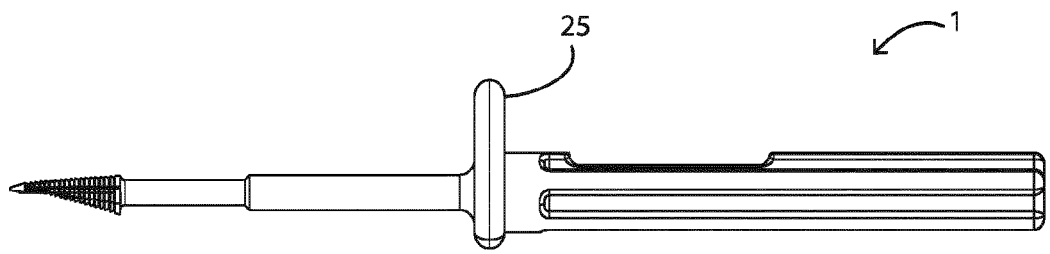
FIG. 5 is a view of a primer tool of the invention.
Figure 6:
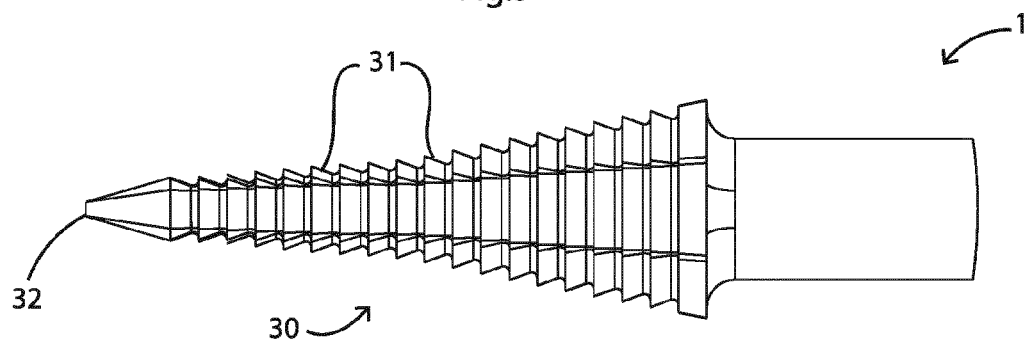
FIG. 6 is an enlarged view of a distal end of the primer tool.

Primer 1 (FIGS. 5 and 6)

Referring to FIG. 5 and FIG. 6 the primer 1 has a cutting head 30 and facilitates the first incision into the metacarpal and eliminates the need for an awl or similar by the surgeon prior to deployment of the first broach 2. In addition, the geometry of the cutting head 30 of the primer 1 is modelled on the geometry of the smallest broach in the tooling set, broach 2. The primer 1 has less bulk, is shorter, has more cutting teeth 31 per unit length and has a much sharper point 32, but has the requisite curved volar, flat dorsal geometry of the broaches and the implant. The primer distal tip does not have a non-toothed bone marrow compacting distal end which is a feature of the broaches. In this case the head 30 has 17 cutting teeth 31, and in general it is preferred that there are in the range of 12 to 22, and more preferably 14 to 20 teeth.

The net effect is that the primer 1 penetrates much farther than an awl or similar, can be used to more precisely locate the initial incision, and most significantly, reduces the effort required with the first broach 2. This is a particularly significant benefit for surgeons with low or reduced hand strength.

Figure 7:
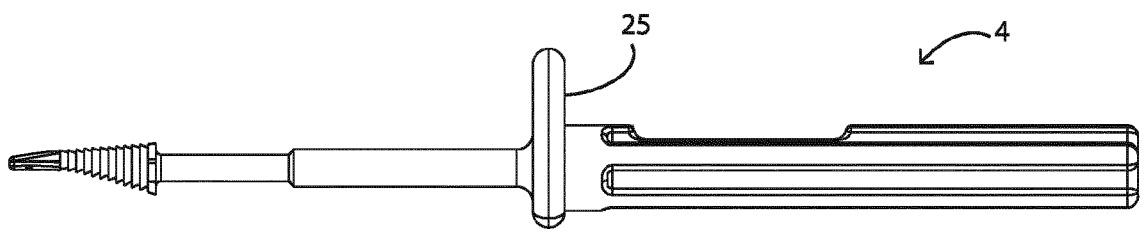
FIG. 7 is a pair of side views of a broach, and different positions of rotation.
Figure 7:
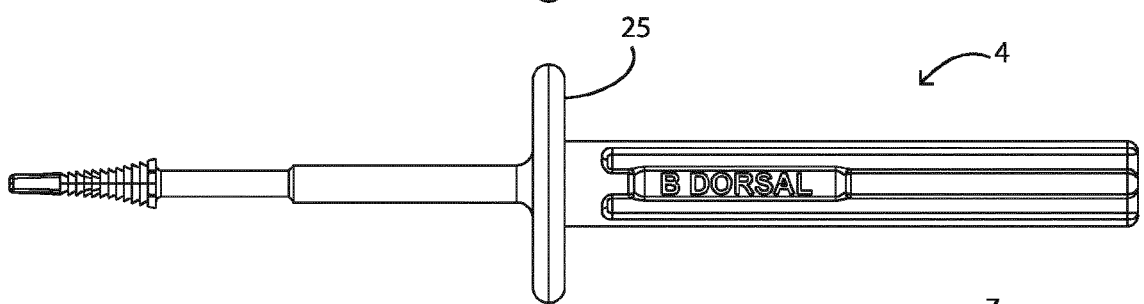

Broaches (FIG. 7)

The broaches 2, 3, 4, 5, 6 (referred to as broaches A to E) are a geometrical match for the implant stems 111. Therefore, the end user can utilize the broaches as trial stems. When the surgeon has completed broaching the metacarpal cavity, there is no need for a separate trial stem to be put in place to assess stem fit as the broach itself will have provided this clinical information.

In addition to the tools described, a trial implant head 70 (FIG. 22) may also be used during the procedure, as described in more detail below.

To install the implant, the primer 1 is used to make the first incision into the metacarpal. By virtue of its cutting teeth density and the fact that the primer geometry closely mimics that of the smallest broach (size A, 2), the primer also aids the surgeon in creating accurate location and orientation of broaches, and hence the stem implant within the metacarpal. One or more of the broaches 2, 3, 4, 5, 6 are then used to broach the metacarpal cavity. Broaches are used in order of increasing size. Thus, size A (2) follows after use of the primer. For any given metacarpal, based on surgeon feel when broaching and/or using X-ray images, the surgeon decides whether successive broach sizes are required. After broaching, the stem insertion tool 9 is used to insert the stem part 110 of the implant into the metacarpal cavity until the metacarpal stem implant 110 is located flush or just proud of the resected metacarpal. This is facilitated by the close relationship of broaches to stem implants, and the surgeon being able to gauge where the base of the stem will end up in relation to the resected metacarpal based on the position of the final broach he or she uses.

Figure 8:
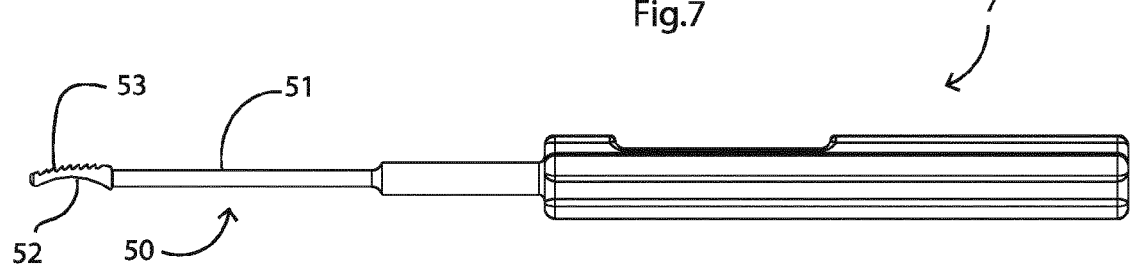
FIG. 8 is a side view of a first dual purpose tool, and FIG. 9 are side and plan views of head of the first dual purpose tool.
Figure 9:
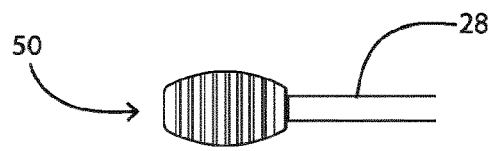
Figure 9:
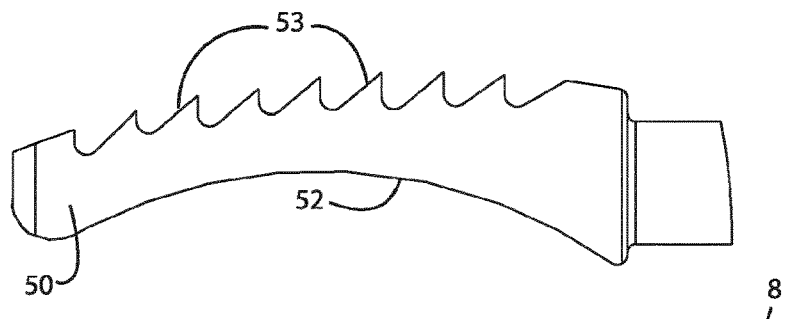

The First Dual Purpose Tool 7 (FIG. 8 and FIG. 9)

Referring to FIGS. 8 and 9, the first dual purpose tool 7 has both rasp 52 and broach 53 features. The rasp 52 on the concave side may be used to sculpt the trapezium bone to the exact radius of the implant head 120. The convex side of the tool 7 carries broach-like teeth 53 which may be used to remove incidental osteophytes or other protuberances encountered in the course of sculpting the trapezium.

As noted above the head 50 of this tool has dual purpose capability. It has a shaft 51 which is tapered, or otherwise reduced in diameter for ease of access to the small joint.

The concave side 52 of the head 50 has rasp construction and is designed for sculpting the trapezium to the shape of the implant head. The convex side 53 has broach construction for removal of osteophytes and is designed to cut on the pull stroke rather than the push.

Other uses include maxillofacial surgery where bone remodeling is required but a surgeon does not want to have to remove and replace tools in succession. For example, the first dual purpose tool 7 may be inserted into a body cavity and used for rasping function, left in situ but rotated 180 degrees, and then be used for broaching or bone remodeling functions.

The tool 7 may be used to modify the geometry of any bone's external or internal surface depending on the geometry of the bone, the cutting surfaces, and the distal end of the tool, with the novel dual function head facilitating ease of use.

The distal end of the tool 7 may be circular, square, flat, or toroidal in shape in accordance with the desired anatomical geometry to be produced by its use.

The distal cross-section above and below the center-line may be of one geometry on one side and another on the other side i.e. toroidal on one side and flat on the other.

Figure 10:
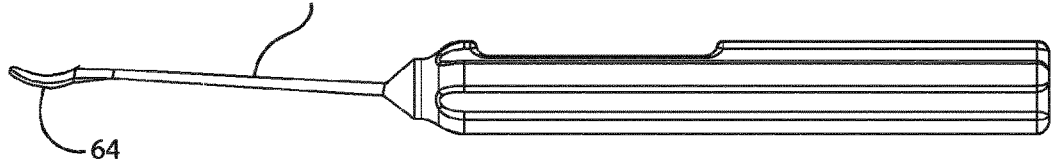
FIG. 10 is a pair of side views of a second dual purpose tool, at different angles of orientation about its axis.
Figure 10:
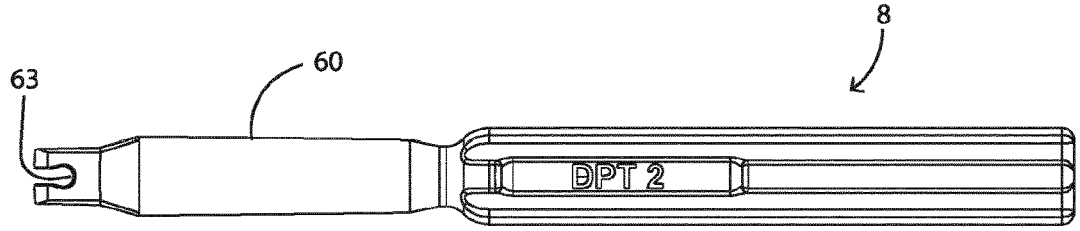
Figure 11:
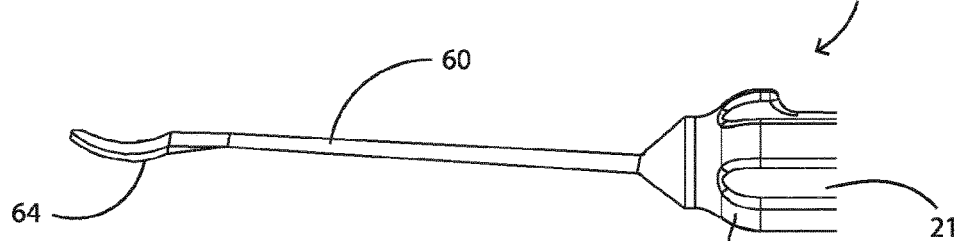
FIG. 11 is an enlarged side view of the head of this tool.
Figure 12:
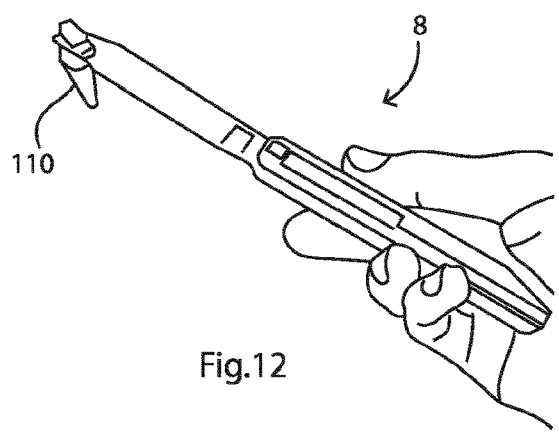
FIG. 12 is a perspective view of the tool in use holding a head and stem construct.
Figure 13A:
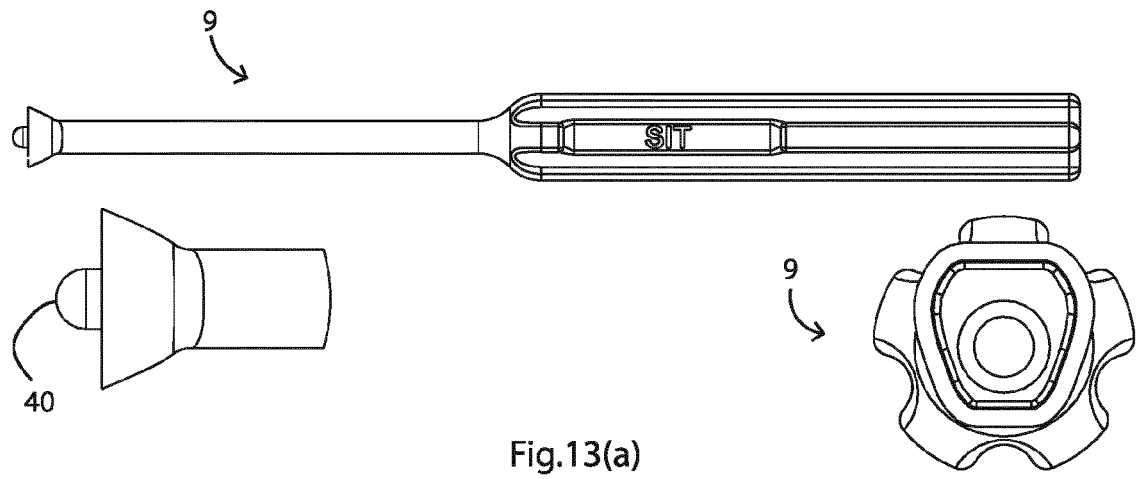
FIGs. 13(a) to 13(c) a full side view, an enlarged side view of a head, and an on-axis end view of a stem insertion tool.
Figure 13B:
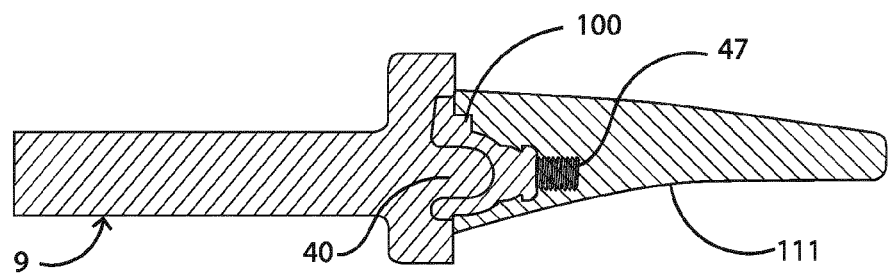
Figure 13C:
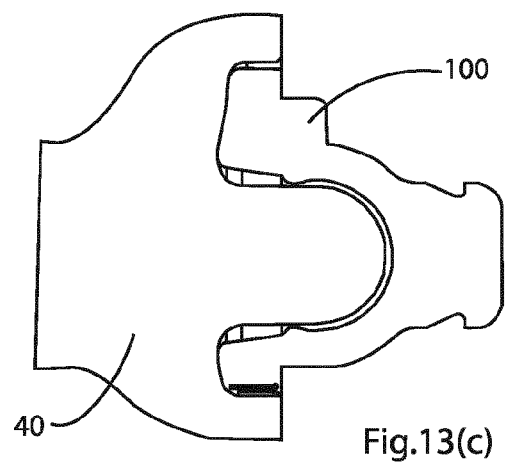

Second Dual-Purpose Tool 8 (FIGS. 10, 11, and 12)

Referring to FIGS. 10, 11, and 12, the second dual purpose tool 8 is used as a metacarpal elevator to move tissue aside and to present the metacarpal to the surgeon for resection. It comprises a stem 60 and a head 64 with a keyhole feature 63. The keyhole feature 63 is at the distal end of the head 64 of the second dual purpose tool 8 and may be used to separate the trial head (70) from the implant stem as illustrated in FIG. 12.

This tool 8 may for example serve as a metacarpal elevator and be used to present the metacarpal to the surgeon for resection. The shaft 60 is flat and is angled with respect to the handle 61 and provides optimum access to both the metacarpal and a fulcrum point location. The head 64 is curved to match the curvature of the metacarpal bone.

In addition, a keyhole slot 63 at the distal end of the head 64 matches the radius of the neck of the implant stem 111 and can be used to lever out a trial head 70 from the liner 100 as illustrated in FIG. 12, when the surgeon is ready to fit the implant head 120. In general, the head of the tool 8 is a claw with a variety of uses as a holder or a gripping lever for remoting an item.

Other uses for the second dual purpose tool 8 include: a) manipulation of any small bone such as the second through fifth metacarpals during surgery; b) removal of plates in small joint surgery by using the tool to leverage the plate off the bone; c) removal of plates with screws in situ where the keyhole can sit around a nail or screw while the plate is leveraged away from the bone; d) removal of screws out of bones where the slot/keyhole 63 is used to leverage screws out of bone which may be of poor quality but where the screw has some fixation.

Stem Insertion Tool 9 (FIGS. 13(*a*), 13(*b*), and 13(*c*))

The internal features of a head 40 of the stem insertion tool 9 captures both the outline and the depth of the liner flange 100 and these features permit the distal portion of the tool head to bottom out on the base of the metacarpal stem implant 111. The distal head 40 of the tool 9 sits on the base of the stem 111. As the surgeon manipulates the stem 111 into the bone, the liner 100 will not be damaged because the forces are transmitted from the metal head of the stem insertion tool 9 to the metal base of the stem 111, should an impactor be used in conjunction with the stem insertion tool 9.

The profile of the distal portion of the tool head 40 exceeds that of the base of the metacarpal stem implant 111. When the metacarpal stem implant 111 has been located flush or just proud of the resected metacarpal, these design features then ensure that the liner 100 cannot be inserted below flush in the bone.

The bullnose at the distal end of the stem insertion tool 9 is less than the internal diameter of the liner 100 at the snap fit location, and because the stem insertion tool 9 closely envelops the exterior of the liner 110, no damage occurs to the snap fit of the liner 110 with the ball of the head 121.

Figure 14A:
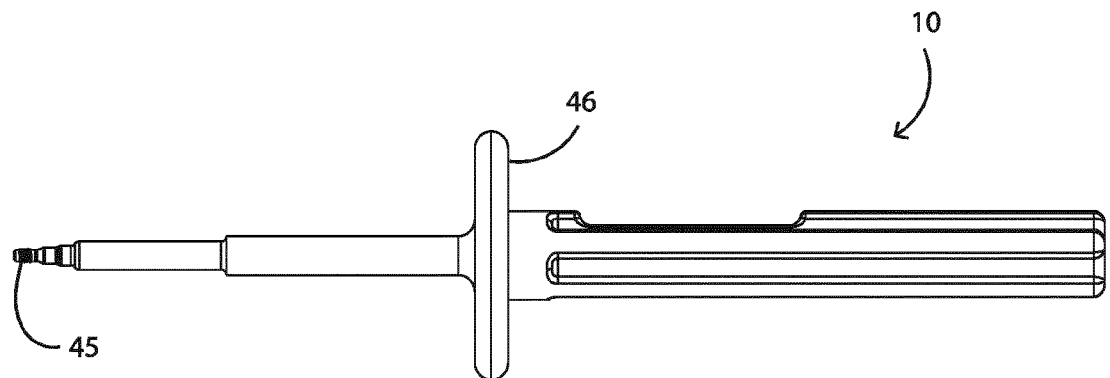
FIG. 14(a) is a side view of a stem exchange tool.
Figure 14B:
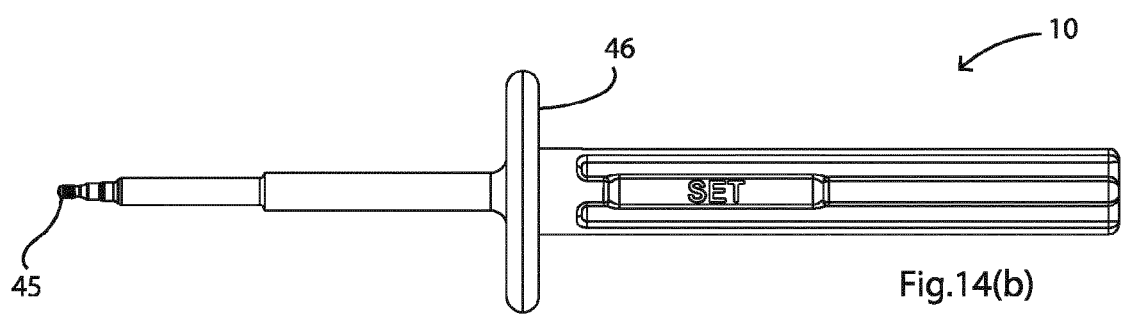
FIG. 14(b) is a plan view of this tool.
Figure 14C:
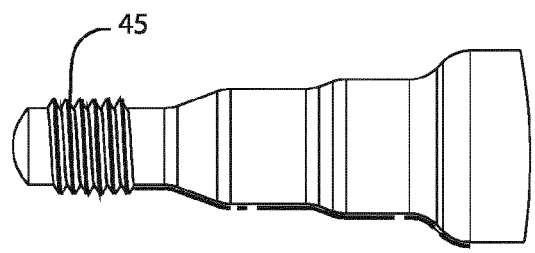
FIG. 14(c) 14(c) is an enlarged side view of the head of the stem exchange tool.

Stem Exchange Tool 10 (FIG. 14(*a*), 14(*b*), 14(*c*))

If necessary, the stem 110 may be removed from the metacarpal cavity using the stem exchange tool 10. If the liner 100 is removed from the stem 110, a fine metric threaded thread 45 of this tool may be engaged with the fine metric threaded thread 47 (see FIG. 13(*b*)) in the stem 111, and if so desired, the stem 111 may be removed. The stem exchange tool 10 has a full round flange 46 for impactor use to aid stem withdrawal, regardless of how deep the threads are engaged with each other.

If a stem 111 is being implanted without a polymeric liner 100, then the stem exchange tool 10 may be used to position the stem 111 and facilitate impaction of the stem 111 into place. The same would hold true for a stem without a polymeric liner, having instead a metal socket with mating threads for the stem exchange tool 10 distal to the socket.

Figure 16:
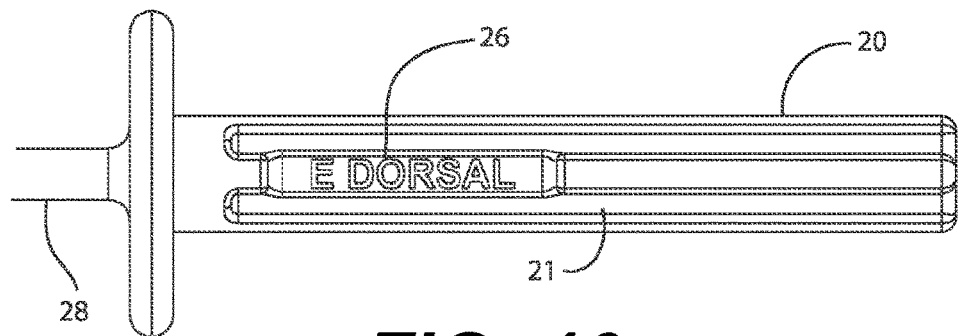
FIG. 16 is an enlarged view of a handle end of some of the tools.
Figure 17:
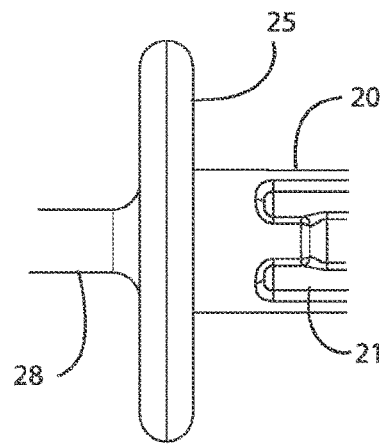
FIG. 17 is an enlarged view of a flange of some of the tools.
Figure 18:
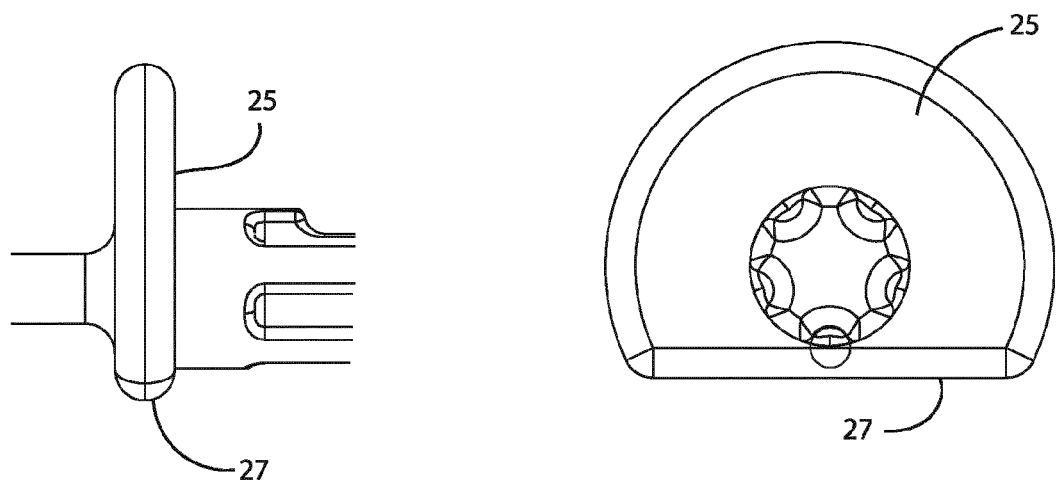
FIG. 18 is a set of detailed images of the flange of some of the tools.

Fluted and Flanged Handles (FIGS. 16 to 18)

Figure 15:
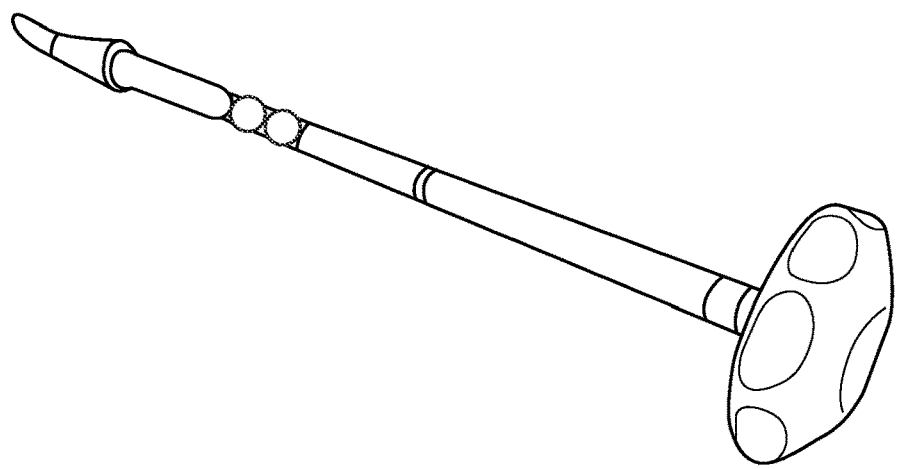
FIG. 15 is an image of a prior art tool.

FIG. 15 illustrates a circular indented handwheel which is at the proximal shaft ends of many prior art orthopaedic broaches. The prior art circular proximal shaft ends (used with impactors for tool removal) are gripped by the surgeon and can promote twisting of the tooling which can lead to larger apertures in the bone than intended. The aperture created by a broach cutting head should correspond to the geometry of the implant. Prior art broaches with the circular type of handles are twisted to gain purchase in the bone.

In the tool set, the tools have plain elongate proximal handles 20 which are fluted 21 to aid grip as illustrated in FIGS. 16 and 17. The tooling therefore promotes axial motion, and this leads to aperture creation in the bone which conforms more exactly to the geometry of the broach cutting head and thus the implant.

The primer 1, the broaches 2, 3, 4, 5, 6 and the stem exchange tool 10 all have flanges 25, 46 at the distal end of the handle 20 as illustrated in FIGS. 16 to 18. The flanges 25 (and 46 on the tool 10) enable an impactor to be used, if required, for tool extraction purposes. They also serve as a stop for the surgeon's hand and, coupled with the flat on the handle which carries the tool identification 26 and serves as a thumb grip, the primer 1 and broaches 2, 3, 4, 5, 6 promote firm axial forward motion.

This means that, in contrast to other tooling, the tooling of the invention requires little or no impacting. This reduces potential fracture damage of the bone during surgery which has been observed in clinical practice with conventional tools.

The flanges 25 of the primer 1 and all broaches 2, 3, 4, 5, 6 are truncated to provide a non-circumferential side edge 27 on the volar aspect at 270° as illustrated in FIG. 18.

This facilitates the surgeon, by enabling the tools to be used at an angle very much in line with the axis of the metacarpal during surgery. This feature also further reduces any tendency for the surgeon to twist the tool, and it also permits ample space on the distal side of the flange for an impactor to aid withdrawal of the tool, should that be required.

Figure 19A:
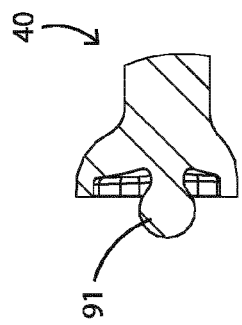
FIGS. 19(a), 19(b), and 19(c) illustrate an alternative stem insertion tool in use.
Figure 19B:
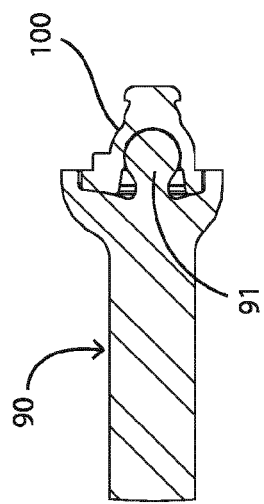
Figure 19C:
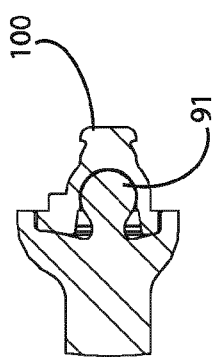

Stem Insertion Tool 90 (FIGS. 19(a), 19(b), and 19(c))

An alternative stem insertion tool 90 incorporates a ball 91 where the diameter is less than that of the implant head ball diameter, but is just sufficient to provide a light snap-fit. This light snap-fit provides attachment between the tool 90 and the implant stem-liner assembly 110, such that the surgeon may use the tool to transport the implant from the preparation area directly to the implant site.

Figure 20A:
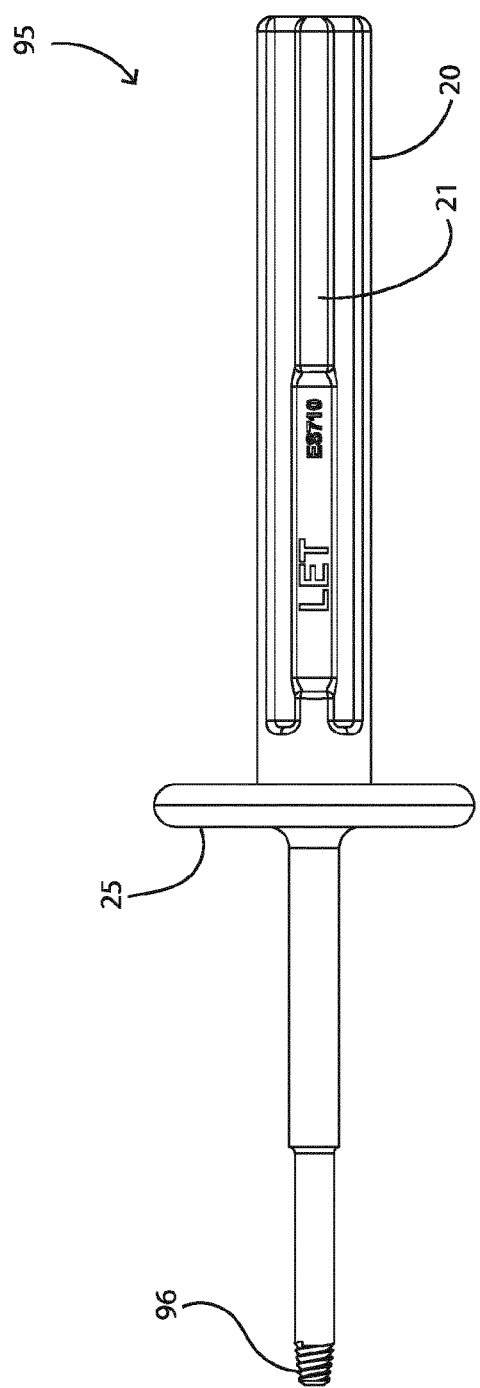
FIG. 20(a) is a side views of a liner exchange tool.
Figure 20B:
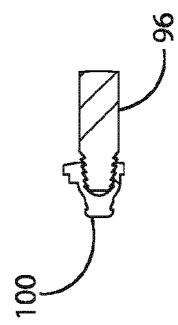
FIG. 20(b) shows a head of the tool engaging a liner.

Liner Exchange Tool 95 (FIGS. 20(a) and 20(b)) The tool set may additionally include a tool 95 to withdraw a liner 100 which has been assembled in a stem 111, which in turn has been implanted in a metacarpal. There may be occasion to withdraw a liner when access to the threaded portion 47 of the stem is required in order to withdraw or exchange the stem. A threaded head 96 of the tool 95 is configured as a double-start tapered thread where the helices of the thread engage with the snap-fit diameter of the socket within the liner 100. The tool 95 is threaded into the liner 100 until resistance is felt at which point the liner 100 is readily levered out of the stem housing 112 (illustrated in FIG. 20(a)).

Figure 21:
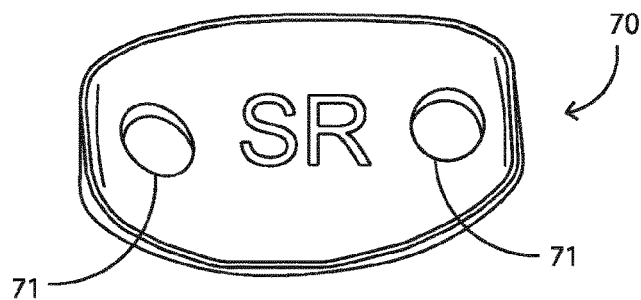
FIG. 21 is a view of a trial head used during an implant installation procedure.

Trial Head 70 (FIG. 21)

The trial head 70 conforms to the geometries of the associated implant head 120, except for having two through holes 71 through the saddle, and having two letter identifications appropriate to each of the four trial head types laser etched onto the base. The through holes 71 aid in differentiating the trial heads 70 from the implant's components 120.

The ball diameter of the trial head 70 is also slightly smaller than the ball diameter of the implant head 120 . . . so that the snap-fit of the liner 100 is not stressed. Although the ball diameter is slightly reduced, the metacarpal to trapezium distraction distance is maintained the same as that of the implant heads 120, by increasing the neck lengths of the trial heads 70.

The use of trial heads 70 in conjunction with the implant stem 111 decreases the number of surgical steps to be successfully completed by the end user. It avoids need for the surgeon to open and use an implant on a trial-and-error bases, by using the trial head 70 to check size firstly before choosing the implant to use.

Figure 22:
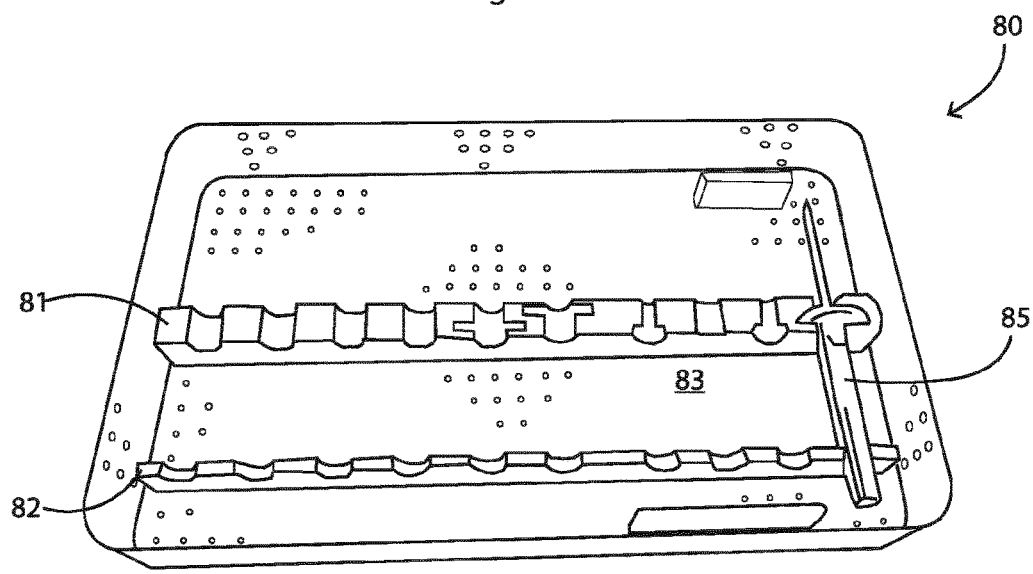
FIG. 22 is a view of an instrument tray.
Figure 23:
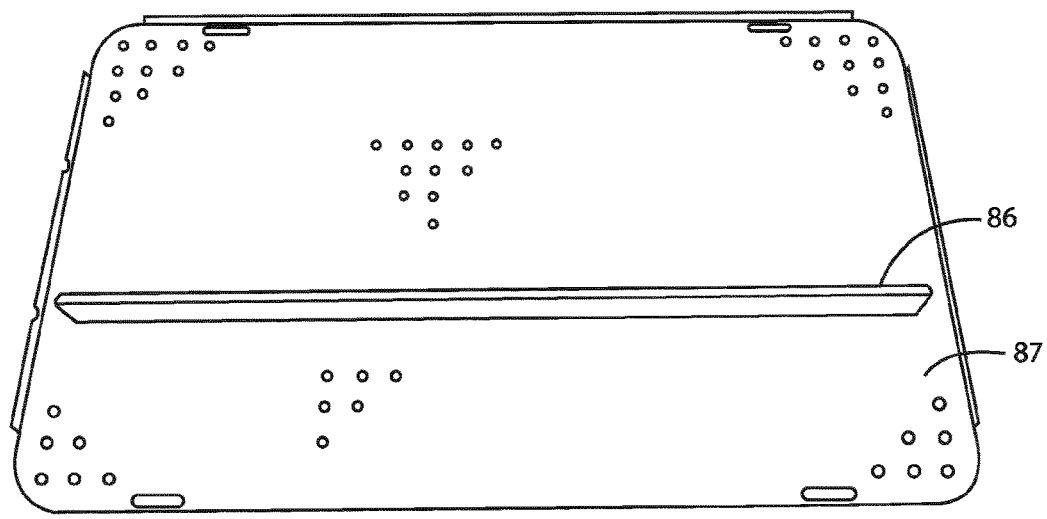
FIG. 23 is a view of a lid for the instrument tray of FIG. 22.

Instrument Tray 80 (FIGS. 22 and 23)

The instrument tray is advantageous in that, rather than containing multiple stand-offs to house individual tools 85, all the tools are located by two strips 81, 82 which may be of the polymer PPSU (polyphenylsulfone), mounted, such as screwed into a base 83 or integrally moulded with the base. The tools (only the tool 85 is shown) are further secured by a single strip 86 attached to the underside of a lid 87, which acts on the thumb grip flats of the handles of the tools. Correct orientation of the lid 87 (and thus the securing strip 86) is ensured by locating two latches closer together on one side of the lid than the other (not shown).

Intra-Operative Assembly Fixture 140 (FIGS. 24(a) and (b))

An assembly fixture 140 may be used in a surgical setting to assemble a liner 100 into a stem 111. A base 141 of the fixture 140 has separate retainers 142 for each of the implant stem sizes. Each retainer 142 has a socket 143 for cradling the distal (narrow) end of the stem 111 to retain it in an upright position. The retainers 141 also have aligned upper through holes for retaining the wider (proximal) ends of the stems 111. Each retainer is sized in increasing size order from left to right for a particular stem size, called Stem A, B, C, D, and E respectively.

The assembly also comprises a pusher 148 with a knurled thumbwheel 149 for rotating a screw 150 with a lower pusher face 151. The screw 150 extends through a pusher body with a pair of parallel dovetails 152 for engaging in corresponding dovetail grooves 145.

A stem 111 is placed vertically in the appropriate retainer 141 . . . a liner 100 is aligned with the universal cap formed by the body 152 of the pusher 148 . . . incorporating a light snap fit as it is fitted to the liner. The pusher 148, when pushed fully home in any one of the sets of slots 145, is positioned such that the centre of the screw 150 is centered over the stem. The screw 150 is then turned to fully push the liner 100 into the stem 111, thereby seating the liner 100 in the stem 111.

Full Tool Listing of One Preferred Example

The following is a listing of all components of a full tool-set apparatus in one example.

| | |
|---|---|
| 1 | Primer |
| 2 | Broach A |
| 3 | Broach B |
| 4 | Broach C |
| 5 | Broach D |
| 6 | Broach E |
| 7 | Rasp |
| 8 | Metacarpal Elevator |
| 9 | Stem Insertion Tool |
| 10 | Stem Exchange Tool |

-continued

| | |
|---|---|
| 95 | Liner Exchange Tool |
| 70 | Trial Head: Short Neck, Regular |
| 70 | Trial Head: Short Neck, Flat |
| 70 | Trial Head: Long Neck, Regular |
| 70 | Trial Head: Long Neck, Flat |
| 140 | Intra Operative Assembly |
| 141 | Fixture Base |
| 148 | Slider |
| 149/150 | Press Screw |
| 152 | Liner Cap |
| 80 | Assembled Tray |
| 80 | Empty Tray |

It will be appreciated that the apparatus described provides major assistance to a surgeon for performing an operation, both in terms of accuracy and reduced time.

The invention is not limited to the embodiments hereinbefore described, which may be varied in construction and detail.

The invention claimed is:

1. A set of tools for installation of an implant into a bone, the set of tools comprising:
a plurality of broaches, wherein the broaches are of different sizes, and each of the broaches have a distal tip and a plurality of cutting teeth along a length thereof,
a priming tool having a distal tip and a plurality of cutting teeth along a length thereof,
wherein the priming tool is shorter than a smallest broach of the plurality of broaches, and has more cutting teeth per unit length than the smallest broach of the plurality of broaches, and
a stem insertion tool having engagement features for engaging with corresponding engagement features of the implant for transmission of forces applied from the stem insertion tool to the implant, wherein the engagement features comprise at least one of a ball configured for snap-fitting into the implant or a bullnose for engaging with the implant.

2. A set of tools as claimed in claim 1, wherein the priming tool and each of the broaches comprise a proximal handle having flutes to aid grip and a flange distal of the proximal handle.

3. A set of tools as claimed in claim 2, wherein the flange is truncated on one side of the handle.

4. A set of tools as claimed in claim 1, wherein a distal head of the priming tool and each of the broaches are curved in a volar direction and are substantially flat in a dorsal direction.

5. A set of tools as claimed in claim 4, further comprising a dual-purpose tool, wherein the dual-purpose tool comprises a head which provides both a rasp and a broach, the head having a first side and a second side opposite to the first side, the first side having a concave shape and comprising rasp features and the second side having a convex shape and comprising broach features.

6. A set of tools as claimed in claim 5, wherein the dual-purpose tool comprises a stem and a head lever for elevation of a bone, the lever having a claw shape and the head comprising a distal engagement slot.

7. A set of tools as claimed in claim 1, further comprising a stem exchange tool, the stem exchange tool comprising a threaded thread for engagement with a threaded socket of the implant.

8. A set of tools as claimed in claim 1, further comprising a liner removal tool to withdraw a liner which has been assembled in the implant, which in turn has been implanted in a metacarpal, wherein the liner removal tool comprises a threaded head configured to engage the liner by rotation of the liner removal tool.

9. A set of tools as claimed in claim 8, wherein the implant comprises an insert for a proximal end of the stem.

10. A set of tools as claimed in claim 1, further comprising (i) at least one trial head for temporary placement in or on a bone or implant part during preparation of the bone to receive an implant head, wherein the trial head has some dimensions that are smaller than those of the implant head, and (ii) a dual purpose tool comprising a stem and a head, the head having a claw shape for elevation of the bone and a slot configured to separate the trial head from the implant.

11. A set of tools as claimed in claim 10, further comprising a plurality of different sized trial heads.

12. A set of tools as claimed in claim 10, wherein the trial head includes a ball for insertion in an implant socket on a trial basis and the ball is smaller than an implant ball for the socket.

13. A set of tools as claimed in claim 10, wherein the trial head includes at least one aperture.

14. A set of tools as claimed in claim 1, further comprising an assembly fixture configured to assemble a liner into the implant, the assembly fixture comprising a plurality of stem retainers for each of a plurality of implant stems, and a pusher device arranged to push a liner into the implant stem upon rotation of a handle.

15. A set of tools as claimed in claim 14, wherein each stem retainer has a socket for cradling a distal end of the implant and an aligned through hole to retain the implant a liner insertion position.

16. A set of tools as claimed in claim 14, wherein the pusher device comprises a screw with a pusher face extending through a pusher body.

17. A set of tools as claimed in claim 16, wherein the pusher body comprises a pair of parallel dovetails for engaging in corresponding dovetail grooves for positioning the pusher screw in alignment with the implant stem in the retainer.

18. A kit comprising a set of tools as claimed in claim 1, wherein the implant includes a stem.

19. A kit as claimed in claim 18, wherein the stem is configured for intramedullary engagement with an end of a first metacarpal bone.

20. A kit as claimed in claim 18, wherein the implant is for a first carpometacarpal joint for spacing a trapezium bone from a first metacarpal bone, the implant comprising a proximal implant part having a saddle-shaped surface for translational movement over the trapezium and the stem is mountable to the proximal part in an articulated coupling.

21. A kit as claimed in claim 20, wherein the articulated coupling is a ball and socket joint and the proximal implant part comprises a head for mounting to the stem.

22. A kit as claimed in claim 1, further comprising a tray configured to house the tools, the tray including a base, a plurality of side walls extending from the base, and tool support strips mounted to the base, wherein the tools are mounted to the support strips in an order in which the tools are to be used in a surgical procedure.

23. A kit as claimed in claim 22, wherein the tray includes a lid, the lid having a strip to engage the tools and retain the position of the tools in the tray.

24. A kit as claimed in claim 23, wherein the strip engages thumb grip flats of the tools.

* * * * *